United States Patent [19]
Yeager et al.

[11] Patent Number: 5,421,867
[45] Date of Patent: Jun. 6, 1995

[54] COMPOSITION AND PROCESS OF COMBINING A GROUT OR MORTAR MIX WITH COPPER-8-QUINOLINOLATE TO FORM AN ANTIMICROBIAL COMPOSITION

[75] Inventors: Charles C. Yeager, Auburn, Calif.; Leo A. Eachus, Coeur d'Alene, Id.; Bruce B. Gullixson, Spokane, Wash.

[73] Assignee: CuCorp, Inc., Spokane, Wash.

[21] Appl. No.: 136,821

[22] Filed: Oct. 18, 1993

[51] Int. Cl.⁶ ...................... C09D 1/08; A01N 33/00; A01N 59/20
[52] U.S. Cl. ................................ 106/18.32; 106/737; 106/819; 106/823; 514/187; 514/499
[58] Field of Search ..................... 106/15.05, 737, 819, 106/823, 18.32; 514/187, 499

[56] References Cited

U.S. PATENT DOCUMENTS

| | | | |
|---|---|---|---|
| 2,689,837 | 9/1954 | Darby et al. | 523/122 |
| 3,784,357 | 1/1974 | Muraoka | 106/18.34 |
| 3,918,981 | 11/1975 | Long | 106/16 |
| 3,998,944 | 12/1976 | Long | 424/413 |
| 4,337,117 | 6/1982 | Bodendorf et al. | 162/161 |
| 4,556,426 | 12/1985 | Chesney, Jr. et al. | 106/18.32 |
| 4,602,011 | 7/1986 | West et al. | 514/187 |
| 4,766,113 | 8/1988 | West et al. | 514/187 |
| 5,000,618 | 3/1991 | Greenley | 405/128 |
| 5,066,328 | 11/1991 | Zlotnik | 106/18.32 |
| 5,129,946 | 7/1992 | Evans | 106/18.3 |
| 5,304,236 | 4/1994 | Fears | 106/15.05 |

FOREIGN PATENT DOCUMENTS 2006183 5/1979 United Kingdom ............. 106/15.05

Primary Examiner—Anthony Green
Attorney, Agent, or Firm—Thomas G. Walsh

[57] ABSTRACT

New and useful cementitious-based products, such as mortar, grout, backerboard and stucco, are all comprised of Portland cement as a common ingredient combined with optional fillers and additives with the addition of an effective antimicrobial agent. In a humid, warm and a poorly circulating air environment, mildew from a fungus, as well as the growth of other microbes will flourish. With the addition of Copper-8-quinolinolate as a fungicide to the cementitious-based mix, a zone of antibiosis is created to inhibit the growth of these organisms for the duration of the products use.

5 Claims, No Drawings

COMPOSITION AND PROCESS OF COMBINING A GROUT OR MORTAR MIX WITH COPPER-8-QUINOLINOLATE TO FORM AN ANTIMICROBIAL COMPOSITION

BACKGROUND OF THE INVENTION

1. Field of the Invention

The invention relates to the general field of incorporating a fungicidal and antimicrobial composition, copper-8-quinolinolate, into building and construction materials and compositions, more specifically, cementitious compositions such as grout, mortar, backerboard and stucco for the purpose of inhibiting and preventing the growth of fungi, such as molds that cause mildew, as well as other microbes.

2. Description of Related Art and Information

Grout, mortar, backerboard and stucco are common cementitious-based construction materials used in the building of a vast majority of all construction and building projects. This includes living and commercial units as well as recreational, industrial, governmental and a variety of other construction ventures. Microbial containment, especially the fungal growth of mold and similar microbes, is always of concern to both contractor and inhabitant. The prevention of sick and contaminated buildings is a worthy environmental goal. Fungi that produce mold frequently grow in damp, poorly ventilated areas causing damage and an unsightly and unhealthy environment.

The floors, walls and ceilings of bath rooms, shower and bathtub stalls, changing rooms, food processing areas, storage rooms and like areas, commonly have tile set in a mortar and grout composition over a cementitious substrate for moisture and water containment and control. Mold and other microbes often grow in these areas. It has been well documented that ventilation and air distribution systems release and spread fungi and other microbes throughout the building environment. This wide spread contamination inoculates wet and difficult to dry areas with spores of fungi as well as other microbes.

A common area of fungus/mold growth causing mildew, are areas that dry slowly, thus allowing spores to germinate and flourish. There is a long felt need to control this unwelcomed contaminate and growth of mold for health and environmental reason.

Mortar, grout, backerboard and stucco are all cementitious products similar in composition but designed, applied and used for different but related objectives. Grout is a thin mortar used for the filling of spaces between tiles and masonry to provide a finish comparatively level with the surfaces of the tiles and masonry, for both aesthetics and ease of maintenance. When the grout solidifies it provides a monolithic structure to the multitude of tiles, bricks or other products that have been grouted. Grout is a bonding agent in that it must bond well into the spaces in which it is applied to.

Mortar is a basic combination of mason's, or fine sand, and Portland or mason's cement used as a bonding agent for the laying of tiles, bricks and other masonry products. Like grout, mortar provides a monolithic structure to the finished installation of masonry products, except for those that require grouting, such as ceramic tiles as well as other tiles known in the art. Mortar is used exclusively as a bonding agent to create the adherence of two separate products, such as tile, to concrete.

Backerboard is a solid sheet of a cementitious material that provides a sound, and stable substrate for the installation of tiles and masonry materials, such as thin brick veneer. Due to the nature of backerboard, being offered in sheet form, which can be nailed to walls, floors and ceilings, interior or exterior, the product eliminates the need for lath and plaster substrates as used in the past. This aspect is a great labor saver to any tile installation process. Backerboard is used only as a substrate to which other products are bonded to, such as with mortars, adhesives and mastics.

Stucco is a mixture of Portland cement and sand. It is applied to both the interior and exterior of buildings as a finished siding. Stucco has many attributes which include long low-maintenance life, integral coloring, therefore, never needing paint, and weatherproofing attributes. Stucco is employed as a decorative and useful siding material.

In the setting of tiles, a proper substrate must first be in place to support the tiles that are then bonded to the substrate. Backerboard is an example of an adequate substrate. An other example is a metal lath with cement plaster applied to it as an "on-site" substrate. With the substrate in place, tiles are set into a mortar composition, well known in the art. Once the mortar has cured, the tile-enclosed facility can then be grouted to fill the open spaces between the tiles. Once the grout has cured, it can then be exposed to moisture and use. Prior to the instant invention, the incorporation of an antimicrobial composition, specifically, copper-8-quinolinolate, into the cementitious compositions of mortar, grout, and backerboard had not been known in the art.

The use of stucco, as a cementitious interior and exterior finish in housing and commercial building construction, is still another use for the present invention in which copper-8-quinolinolate is incorporated into the stucco mix prior to its use and curing as a building siding. This new composition of a stucco-containing fungicide prevents the growth of fungus causing mildew on stucco.

The use of fungicides in various forms in the building and construction industry is known in the art. U.S. Patent No. 5,066,328 to Zlotnik, Antimicrobial Coating, is directed to an antimicrobial mixture of Copper-8-quinolinolate mixed with a binder composition that imparts sufficient fluidity to the copper-8 composition to permit the mixture to be applied as a liquid which will adhere to air passageways such as metal, fiberglass or plastic media in heating, air-conditioning and ventilation duct work for the prevention of fungal and other microbial growth. The Zlotnik invention is significantly different from the present invention in that it neither discloses, suggests nor claims the use of an antimicrobial in cementitious based products.

U.S. Pat. No. 3,784,357 to Muraoka, Protective Surfaces or Liners for Subaqueous Structures, discloses the incorporation of a choice of several chemical fungicides, including copper-8-quinolinolate, into an expanded marine shale aggregate to protect sub-aqueous concrete walls, pipes and slabs from the growth of marine-fouling organisms. Concrete is significantly different from mortar, grout, backerboard and stucco because of its composition and additives, the proportions and ratios of concrete's various elements, the large aggregate size and the uses of concrete. Muraoka does not suggest or disclose the use of antimicrobial compositions incorporated into mortar, grout, backerboard or stucco.

U.S. Pat. No. 4,556,426 to Chesney, Jr. et al., Fungicidal Grout Compositions, discloses the use of a halogenated aromatic dinitrile composition added as a fungicidal ingredient that is combined with the dry ingredients of a Portland cement grout to form a grout composition used for grouting and setting of ceramic tile. The Chesney Jr. et al. patent does not disclose, suggest or claim the use of Copper-8-quinolinolate in a grout composition for fungicidal control.

There are several U.S. Patents that have combined antimicrobials and microbiocides, more specifically, copper-8-quinolinolate, into various products, including wood, timber, cloth, concrete, rope, paper, gypsum wallboard, synthetic sheet materials in shoe construction, marine anti-fouling paint, thermoplastic resin compositions, mops and mats, fishnet and other marine structures, geotextiles in landfills, and soaps.

As the above patents disclose, copper-8-quinolinolate, as a well known fungicide, has been incorporated into a variety of products. It is an antimicrobial agent that has a low toxicity to plant and animal life. Public concern regarding toxic fungicides used in the food and ecological chains, has put pressure on governmental agencies to control, and in many cases, eliminate these agents. Examples of toxic fungicides are compounds of toxic metals such as mercury and lead, and organic compounds such as chlorinated phenols, all of which have had an adverse effect on the environment. Phenylmercury fungicides have been added to grout compositions in the past but increasing concern as a health hazard has all but eliminated their use.

The expensive halogenated aromatic dinitriles, combined with grout to give fungicidal activity, has not achieved the expectations or effectiveness once thought, leaving the field void of a safe, useful, practical, and effective antimicrobial that can be easily, inexpensively and effectively incorporated into mortar, grout, backerboard and stucco compositions. This lack of success of incorporating a fungicide into a tile setting system and other uses of cementitious compositions such as stucco, is illustrative of a long felt need for such compositions.

It is an object of the present invention to provide a new, useful and improved mortar, grout, backerboard and stucco compositions, all cementitious-based, containing an antimicrobial agent, that can be used in the installation of ceramic, glass, stone and marble tiles as well as any other tile products requiring mortar, grout or backerboard, or for exterior and interior stucco plaster coatings. The new mortar, grout and backerboard compositions of the present invention can also be used in non-tile areas where this new composition is indicated for the inhibition of microbes.

SUMMARY OF THE INVENTION

This new and useful invention provides an improved fungicidal mortar, grout, backerboard and stucco compositions for use in the setting of tile of a variety of sources, such as ceramic, glass, stone, brick and marble as well as for stucco plaster coatings. The new composition can also be used in areas requiring the use of a mortar, grout or backerboard but where tile is not required. The mortar, grout, backerboard and stucco compositions are comprised of a Portland cement base with a predetermined amount of copper-8-quinolinolate added. The copper-8 can be combined with either a dry mix of a mortar or grout composition with water added to the mix to form a workable mixture, or, in the alternative, liquid copper-8 suspended in water can be combined with the composition, to form a workable mixture.

There are several additives that can be combined with the wet or dry grout, mortar, backerboard or stucco mixes for the purpose of bringing certain properties to the mix. These additives include cellulose, acrylic, latex and coloring, as well as any other additives known in the art. Cellulose, with its hygroscopic property, aids in retaining moisture, thereby improving the workability of the mix and averting cracking by extending the curing time. The acrylic and latex, as synthetic polymer additives, give the mix an improved bond strength and adds elasticity. Coloring is for aesthetics and does not effect the properties of the mix. When copper-8 is added to a white mix of grout, there is a slight greenish tint or stain, however, in mixes that have coloring added, this is not perceived. With the addition of titanium dioxide, the whiteness of the mortar or grout mix is improved.

With copper-8-quinolinolate fungicide incorporated into a cured mortar, grout, backerboard or stucco composition, the fungicide leaches in water at a nearly insoluble rate of 0.8 ppm, inhibiting fungal and bacterial growth for the duration of the product. It is this extremely slow leaching rate that allows for the fungicidal efficacy. The low solubility in water creates a zone of fungicidal activity, deterring the growth of fungi and bacteria on tile surfaces, exposed grout areas, bonding mortars, backerboard substrate and stucco surfaces. Due to this extremely low leach rate, copper-8-quinolinolate remains effective as a fungicide in grout, mortar, backerboard and stucco for the life of the applications of these products.

DETAILED DESCRIPTION OF THE INVENTION

This new and useful invention has the significant property of preventing the growth of microbes, specifically fungi and bacteria, in wet and damp areas frequently subject to microbial growth. Mortar, grout, backerboard and stucco products that incorporate copper-8-quinolinolate are especially desirable because they have excellent wetting characteristics including ease of use and inhibition of fungal and bacterial growth for the duration of the product.

In a preferred embodiment, a blend of grout mix is prepared. The mix is comprised of a 50 to 99% by weight of Portland cement, fine silica sand as an optional filler and any other number of insoluble filler materials known in the art. Grout may also contain, if required, any of several desirable additives, said additives and fillers having a range of between 0% to about 50% by weight of additives and/or fillers known in the art. The grout combination may also contain from about 0.2% to about 0.5% by weight of a hygroscopic agent known in the art. The grout mix may also contain form 0% to about 10% by weight of a coloring agent.

The grout mix is then combined with water containing a 0.1 to 15% by weight suspension of copper-8-quinolinolate, preferably 0.5% by weight, to form a workable mix consistent with that required to set and grout tile. Examples of filler materials which may be employed are crushed glass, silica, barytes, alumina, various clays, diatamaceous earth, and other similar inert materials such as wollastonite, mica, flintpowder, kryolite alumina trihydrate, talc, sand, pyrophyllite, blanc fixe, granulated polyethylene, zinc oxide and mixes thereof known in the art.

In another preferred embodiment, copper-8-quinolinolate is combined with a mortar mix. A dry mix of mortar, comprising Portland cement, sand and any number of optional additives, such as latex, which gives greater bonding strength and adds elasticity, is combined with water containing a 0.1 to 15% by weight suspension of copper-8-quinolinolate, preferably 0.5% by weight, to form a workable mortar mix. The mortar can then be used for the purpose intended, for example, setting tile or bricks as well as finishing walls, decorative sites, or any other such uses in which a mortar mix is employed.

A further preferred embodiment of this new and useful invention is the incorporation of copper-8-quinolinolate into a cementitious backerboard. Backerboard, a prefabricated foundation board comprised of Portland cement, sand, small aggregate, and a fiber glass mesh cloth, is formed in a continuous process of aggregated Portland cement slurry and reinforced with glass fiber mesh imbedded on both surfaces. Backerboard serves as a substrate for which the tile is bonded to the backerboard with a mortar mix. It can be applied to supporting wall studs, over sheets of dry wall or plywood material, and can be fixed to floor and ceiling joists. It is manufactured under various trade names, such as for example, GLASSCRETE, WONDERBOARD, DUROCK, UTIL-A-CRETE and HARDIBOARD.

During the backerboard manufacturing process, copper-8-quinolinolate, in a concentration of from a 0.1 to 15% by weight suspension in water, preferably 0.5% by weight, is combined with the backerboard slurry mix thereby incorporating the fungicide into the substrate.

Stucco, an additional preferred embodiment, is another cementitious product that, for example, can be comprised of mason's sand, from about 40% to about 70% by weight, wetable Portland cement from about 30% to about 60% by weight and any other desirable elements from a selection of additives known in the art. A commonly used and preferable stucco mix is comprised of Portland cement 60% by weight and sand, 35% by weight. Copper-8-quinolinolate is combined with the stucco slurry as either a dry powder or as a liquid dispersed in water at 0.1 to 15% by weight, preferably, 0.5% by weight.

The most important component of these new and improved cementitious products of mortar, grout, backerboard and stucco mixes, is the fungicidal activity resulting from the addition of a copper-8-quinolinolate dispersion in water combined with either wet or dry mixes.

This heavily bonded copper-8-quinolinolate has the formula of $Cu(C_9H_6NO)_2$ with a molecular weight of 354.83:

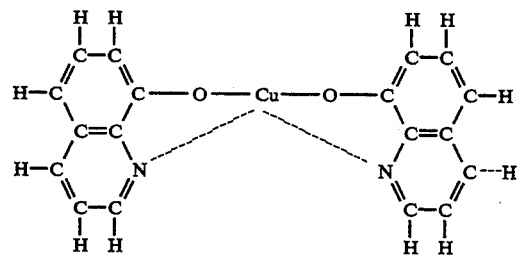

The chemistry and preparation of Copper-8-quinolinolate compound is as follows: Copper-8-quinolinolate is formed by the chelating properties of 8-hydroxyquinoline. 8-hydroxyquinoline has been used to extract heavy metals from various liquids. The bonding is so strong, that the resulting compounds can be easily filtered out, leaving a metal-free liquid.

In the 1940's, it was found that the copper salt of 8-hydroxyquinoline, a compound with low solubility, was an excellent fungicide. It could be applied to textiles by first treating the fabric with 8-hydroxyquinoline and then retreating with a copper salt such as copper acetate. The copper would be grabbed by the 8-hydroxyquinoline already in the fabric forming a powdered copper-8-quinolinolate in the fabric.

The present invention is concerned with the application of the above described mortar, grout, backerboard and stucco workable mixes containing copper-8-quinolinolate that can be used as either a composition in setting and grouting tile for the purpose of inhibiting and preventing the growth of microbes or can be used as a stucco siding. The composition with the copper-8 binds well to the edge and back of ceramic tile. In the setting of a plurality of tiles, the tiles are set into a trowelable copper-8 containing mortar mix in the desired edge to edge relationship on the substrate. The tiles are then allowed to cure in place. After the curing process is complete, the spaces between the tiles are filled with a grout-containing copper-8-quinolinolate according to the present invention.

The composition forms a hard, adherent, microbe-/fungus-resistant bond between the back of the tiles and substrate or backerboard, as well as between the tiles and within the backerboard.

The following example is provided to illustrate the efficacy of incorporating copper-8-quinolinolate into mortar, grout, backerboard or stucco for the purpose of inhibiting the growth of fungus and other microbes. The example is not to be construed as limiting the invention as there are many variations and equivalents which are possible without departing form the spirit or scope of the invention.

EXAMPLE I

The Resistance of Tile Materials to Mildew

Seven tile samples labeled C (control with no copper-8), U, V, W X Y, and Z were treated with copper-8-quinolinolate individually, from 0.25 to 0.75% by weight and then coated with a soap film. The tile, mortar and grout samples were submitted to an independent testing lab for evaluation of resistance to fungal growth and fungus-producing mildew on the mortar, grout and other components of the tile assemblies.

SUMMARY

In a 90 day humidity chamber test, to determine the relative susceptibility of the samples to fungal growth, the tiles were coated on the grout top-side and on the sides with a thin layer of dextrose agar. In the agar overlay test, tile sample C (control) developed heavy fungal growth on the grout, bonding mortar, and on the backing substrate. Light growth was found on the bonding mortar layer of samples U, V, and W. All samples showed some growth on the untreated backerboard substrate, which interfered in the evaluation of the bonding mortars resistance to fungal growth.

Tile samples U, V, W, X, Y, and Z were all resistant to fungal growth on the grout. Samples X, Y, and Z also had no visible growth on the copper-8 containing mortar or grout.

RESULTS

1. Humidity Chamber Exposure

The soap-coated tile samples were inoculated with a mixed fungal spore suspension comprised of:

*Aspergillus niger*, ATCC 9642; *Penicillium pinophilium*, ATCC 9644; *Chaetomium globosum* ATCC 6205; *Aureobasidium pullulans*, ATCC 9348; and *Gliocladium virens*, ATCC 9645

The samples were then placed in a humidity chamber with a relative humidity of 95±5% and a temperature of 86°±2° F. After 30, 60 and 90 days, the samples were examined microscopically at 30× magnification for fungal growth.

After 90 days exposure in the humidity chamber, no detectable fungal growth was found on the grout or other parts of the samples U, V, W, X, Y and Z. There was an abundance of fungal growth on C, the non-treated control sample.

2. Agar Overlay Test

A thin layer of dextrose-mineral salts agar was placed over the grout and on the sides of all tile samples which had been in the humidity chamber for 90 days. These samples (without any additional inoculation) were placed on mineral-salts agar plates and incubated at 28° C.

TABLE I

AGAR OVERLAY METHOD FUNGAL GROWTH

| Tile Sample | | Top Surface Grout | Sides Mortar |
|---|---|---|---|
| C | Control No Cu-8 | Heavy Growth | Heavy Growth |
| U | ¼% Cu-8, grout | No Growth | Light Growth |
| V | ½% Cu-8, grout | No Growth | Light Growth |
| W | ¾% Cu-8, grout | No Growth | Light Growth |
| X | ¼% Cu-8 in grout & mortar | No Growth | Light Growth |
| Y | ½% Cu-8 in grout & mortar | No Growth | No Growth |
| Z | ¾% Cu-8 in grout & mortar | No Growth | No Growth |

The exact elements or combinations of elements, as well as the percentages of elements that these cementitious materials are comprised of are not critical regarding fungicidal efficacy as long as the fungicidal content of copper-8-quinolinolate of the overall composition approaches a range of about 0.1% to about 15%, preferably 0.5%, by weight.

Finally, although the invention has been described with reference of particular means, materials and embodiments, it is to be understood that the invention is not limited to the particulars disclosed and extends to all equivalents within the scope of the claims.

What is claimed is:

1. A grout or mortar cementitious composition comprising a mixture of:
   a. Portland cement present in an amount of from about 50 to 99% by weight;
   b. fine silica sand present in an amount of from about 0 to 50%; and
   c. an aqueous suspension of copper-8-quinolinolate having a molecular weight of 354.83.

2. A composition according to claim 1 wherein the copper-8-quinolinolate is present in an amount of from about 0.25 to 0.5% by weight on a dry basis.

3. The cementitious composition of claim 1, wherein the mixture has set a sufficient time to harden.

4. A process of formulating a grout or mortar cementitious composition comprising mixing:
   a. Portland cement, wherein said cement is present in an amount of 50 to 99% by weight;
   b. fine silica sand present in an amount of from about 0 to 50% by weight; and
   c. a suspension of copper-8-quinolinolate in water, and curing the resultant mixture.

5. The The process according to claim 4 wherein the copper-8-quinolinolate is present in an amount of from about 0.25 to 0.5% by weight on a dry basis.

* * * * *